United States Patent
Poigny et al.

(10) Patent No.: US 9,493,421 B2
(45) Date of Patent: Nov. 15, 2016

(54) ACRIDINEDIONE DERIVATIVES FOR TREATING PIGMENTATION DISORDERS AND AGEING OF THE SKIN

(71) Applicant: PIERRE FABRE DERMO-COSMETIQUE, Boulogne-Billancourt (FR)

(72) Inventors: Stéphane Poigny, Saubens (FR); Françoise Belaubre, Villeneuve Tolosane (FR)

(73) Assignee: PIERRE FABRE DERMO COSMETIQUE, Boulogne-Billancourt (FR)

( * ) Notice: Subject to any disclaimer, the term of this patent is extended or adjusted under 35 U.S.C. 154(b) by 0 days.

(21) Appl. No.: 14/367,727

(22) PCT Filed: Dec. 21, 2012

(86) PCT No.: PCT/EP2012/076681
§ 371 (c)(1),
(2) Date: Jun. 20, 2014

(87) PCT Pub. No.: WO2013/093019
PCT Pub. Date: Jun. 27, 2013

(65) Prior Publication Data
US 2014/0348768 A1 Nov. 27, 2014

(30) Foreign Application Priority Data

Dec. 21, 2011 (FR) ...................................... 11 62204

(51) Int. Cl.
*C07D 219/06* (2006.01)
*A61Q 5/08* (2006.01)
*A61K 8/49* (2006.01)
*A61Q 19/02* (2006.01)
*A61Q 19/08* (2006.01)

(52) U.S. Cl.
CPC .......... *C07D 219/06* (2013.01); *A61K 8/4926* (2013.01); *A61Q 5/08* (2013.01); *A61Q 19/02* (2013.01); *A61Q 19/08* (2013.01); *A61K 2800/40* (2013.01)

(58) Field of Classification Search
CPC ............... C07D 219/06; A61K 8/4926; A61K 2800/40
USPC ............................ 546/102; 514/297; 424/62
See application file for complete search history.

(56) References Cited

PUBLICATIONS

English abstract DN 132:194341. El Shaw M et al.*
Hua Guo-Ping et al. One-pot Synthesis of 10-Methyl-1,2,3,4,5,6,7,8,9,10-decahydroacridine-1,8-dione Derivatives under Microwave Heating without Catalyst, 2005.*
Microwave assisted synthesis of hydropyridines and study of the DPPH-scavenging activity. Feb. 2012, Julio Montes-Avila et al.*
Ashokkumar et al., "Specific $Ca^{2+}$ Fluorescent Sensor: Signaling by Conformationally Induced PET Suppression in a Bichromophoric Acridinedione", European Journal Organic Chemistry, 2009, pp. 5941-5947, XP-002673808.
French language International Search Report (Forms PCT/ISA/220 and PCT/ISA/210), dated Feb. 1, 2013, for International Application No. PCT/EP2012/076681.
French Preliminary Search Report, dated Jul. 24, 2012, for French Application No. 1162204.
Hansch et al., " Exploring QSAR—Fundamentals and Applications in Chemistry and Biology", American Chemical Society, Washington, 1995, pp. ix-xii.
Hansch et al., "The Linear Free-Energy Relationship between Partition Coefficients and the Aqueous Solubility of Organic Liquids", The Journal of Organic Chemisty, vol. 33, No. 1, Jan. 1968, pp. 347-350.
Jorgensen et al., "Prediction of drug solubility from structure", Advanced Drug Delivery Reviews, vol. 54, 2002, pp. 355-366.
Manjashetty et al., "Microwave assisted one-pot synthesis of highly potent novel isoniazid analogues", Bioorganic & Medicinal Chemistry Letters, vol. 21, 2011 (Available online Feb. 2, 2011), pp. 2125-2128, XP-28162350A.
Sangster, "Octanol-Water Partition Coefficients: Fundamentals and Physical Chemistry", Wiley Chichester, 1997, pp. 114-156.

* cited by examiner

*Primary Examiner* — Rita Desai
(74) *Attorney, Agent, or Firm* — Birch, Stewart, Kolasch & Birch, LLP

(57) ABSTRACT

The present invention relates to a compound of general formula (I) in which: —$R_1$ and $R_2$ are simultaneously or independently H, OH, $OCH_3$ or a $C_1$-$C_5$ alkyl radical, —$R_3$ and $R_4$ are simultaneously $CH_3$, —or $R_3$ is H and $R_4$ is $CH_3$, $CH_2CH_3$ or an isopropyl radical or a phenyl radical, —$R_5$ is a $C_4$-$C_{24}$ alkyl radical or a 3-phenylpropanyl or 2,2-diphenylethanyl radical.

7 Claims, No Drawings

ACRIDINEDIONE DERIVATIVES FOR TREATING PIGMENTATION DISORDERS AND AGEING OF THE SKIN

The present invention concerns acridinedione derivatives and topical compositions containing the same, their method of preparation and uses thereof in particular as medicinal product or cosmetic active ingredient.

The subject of the invention is therefore a compound of following general formula (I):

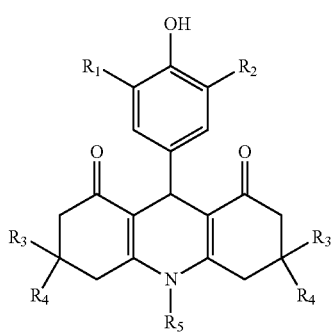

(I)

where:
$R_1$ and $R_2$ simultaneously or independently are H, OH, $OCH_3$ or a $C_1$-$C_5$ alkyl radical,
$R_3$ and $R_4$ are simultaneously $CH_3$,
or $R_3$ is H, and $R_4$ is $CH_3$, $CH_2CH_3$ or an isopropyl radical, or phenyl radical,
$R_5$ is: a $C_4$-$C_{24}$ alkyl radical or 3-phenylpropanyl or 2,2-diphenylethanyl radical.

By <<alkyl radical>> in the meaning of the present invention is meant an aliphatic, saturated, straight-chain or branched hydrocarbon chain having the specified number of carbon atoms. Mention can be made for example of methyl, ethyl and propyl. The alkyl radical may in particular represent the hydrocarbon chain of a $C_1$-$C_{24}$ saturated fatty acid, in particular $C_{10}$-$C_{24}$.

The saturated fatty acids may be capric acid (10:0), undecylic acid (11:0), lauric acid (12:0), tridecylic acid (13:0), myristic acid (14:0), pentadecylic acid (15:0), palmitic acid (16:0), margaric acid (17:0), stearic acid (18:0), nonadecylic acid (19:0), arachidic acid (20:0), heneicosanoic acid (21:0), behenic acid (22:0), tricosanoic acid (23:0), lignoceric acid (24:0). In particular, the saturated fatty acids may be palmitic acid and stearic acid.

According to one particular embodiment of the invention, the compounds of general formula (I) are those in which $R_1$ is H and $R_2$ is $OCH_3$.

Preferably, the compounds of general formula (I) are those in which $R_1$ is H, $R_2$ is $OCH_3$; and $R_3$ and $R_4$ simultaneously represent $CH_3$.

The compounds of general formula (I) can be chosen from the list of following compounds:
10-dodecyl-9-(4-hydroxy-3-methoxyphenyl)-3,3,6,6-tetramethyl-3,4,6,7,9,10-hexahydroacridine-1,8(2H,5H)-dione (Example 1);
10-decyl-9-(3,4-dihydroxyphenyl)-3,3,6,6-tetramethyl-3,4,6,7,9,10-hexahydroacridine-1,8(2H,5H)-dione (Example 3);
9-(3,4-dihydroxyphenyl)-10-methyl-3,6-diphenyl-3,4,6,7,9,10-hexahydroacridine-1,8(2H,5H)-dione (Example 5);
10-decyl-9-(3,4-dihydroxyphenyl)-3,6-diphenyl-3,4,6,7,9,10-hexahydroacridine-1,8(2H,5H)-dione (Example 6);
10-decyl-9-(4-hydroxy-3,5-dimethoxyphenyl)-3,3,6,6-tetramethyl-3,4,6,7,9,10-hexahydroacridine-1,8(2H,5H)-dione (Example 7);
10-dodecyl-9-(3,5-di-tert-butyl-4-hydroxyphenyl)-3,3,6,6-tetramethyl-3,4,6,7,9,10-hexahydroacridine-1,8(2H,5H)-dione (Example 8);
10-dodecyl-9-(4-hydroxy-3-methoxyphenyl)-3,6-diisopropyl-3,4,6,7,9,10-hexahydroacridine-1,8(2H,5H)-dione (Example 9);
10-butyl-9-(4-hydroxy-3-methoxyphenyl)-3,3,6,6-tetramethyl-3,4,6,7,9,10-hexahydroacridine-1,8(2H,5H)-dione (Example 14);
9-(4-hydroxy-3-methoxyphenyl)-3,3,6,6-tetramethyl-10-pentyl-3,4,6,7,9,10-hexahydroacridine-1,8(2H,5H)-dione (Example 15);
10-hexyl-9-(4-hydroxy-3-methoxyphenyl)-3,3,6,6-tetramethyl-3,4,6,7,9,10-hexahydroacridine-1,8(2H,5H)-dione (Example 16);
10-heptyl-9-(4-hydroxy-3-methoxyphenyl)-3,3,6,6-tetramethyl-3,4,6,7,9,10-hexahydroacridine-1,8(2H,5H)-dione (Example 17);
9-(4-hydroxy-3-methoxyphenyl)-3,3,6,6-tetramethyl-10-octyl-3,4,6,7,9,10-hexahydroacridine-1,8(2H,5H)-dione (Example 18);
9-(4-hydroxy-3-methoxyphenyl)-3,3,6,6-tetramethyl-10-nonyl-3,4,6,7,9,10-hexahydroacridine-1,8(2H,5H)-dione (Example 19);
9-(4-hydroxy-3-methoxyphenyl)-3,3,6,6-tetramethyl-10-undecyl-3,4,6,7,9,10-hexahydroacridine-1,8(2H,5H)-dione (Example 20)
10-benzyl-9-(4-hydroxy-3-methoxyphenyl)-3,3,6,6-tetramethyl-3,4,6,7,9,10-hexahydroacridine-1,8(2H,5H)-dione (Example 21);
9-(4-hydroxy-3-methoxyphenyl)-3,3,6,6-tetramethyl-10-(3-phenylpropyl)-3,4,6,7,9,10-hexahydroacridine-1,8(2H,5H)-dione (Example 23);
10-(2,2-diphenylethyl)-9-(4-hydroxy-3-methoxyphenyl)-3,3,6,6-tetramethyl-3,4,6,7,9,10-hexahydroacridine-1,8(2H,5H)-dione (Example 24).

The present invention also extends to the compounds of general formula (I'):

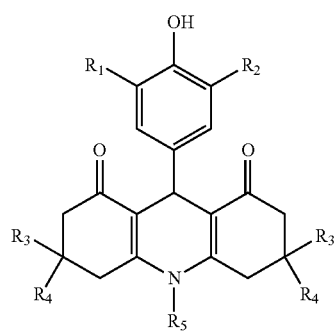

(I')

where:
$R_1$ and $R_2$ simultaneously or independently are H, OH, $OCH_3$ or $C_1$-$C_5$ alkyl radical;
$R_3$ and $R_4$ are simultaneously $CH_3$;
or $R_3$ is H and $R_4$ is $CH_3$, $CH_2CH_3$, an isopropyl radical, or phenyl radical;
$R_5$ is: H, $C_1$-$C_{24}$ alkyl:radical, benzyl radical, phenethyl radical or 3-phenylpropanyl or 2,2-diphenylethanyl radical,
for topical use thereof intended to modify skin pigmentation and in particular as medicinal product or cosmetic active ingredient.

The invention also concerns the compounds of general formula (I') defined above for topical use thereof intended to modify pigmentation of the skin and/or head hair and/or body hair.

The invention further concerns the above-defined compounds of general formula (I') which, when they have a value of log P>4, are generally used for depigmentation of the skin and/or head hair and/or body hair.

The invention further concerns the above-defined compounds of general formula (I') which, when they have a value of log P<3.5, are generally useful for propigmentation of the skin and/or head hair and/or body hair.

Log P, also called Log Kow, is a measurement of the differential solubility of chemical compounds in two solvents (octanol/water partition coefficient).

Log P is equal to the logarithm of the ratio of the concentrations of the examined substance in octanol and in water. Log P=Log($C_{oct}/C_{water}$). With this value it is possible to assess the hydrophilic or hydrophobic (lipophilic) nature of a molecule. If Log P is positive and very high, this means that the molecule under consideration is much more soluble in octanol than in water, which reflects its lipophilic nature, and conversely. A value of Log P=0 means that the molecule is distributed equally between the two phases and $C_{oct}=C_{water}$ (C. Hansch, J. F. Quinlan, G. L. Lawrence, Linear free energy relationship between partition coefficients and the aqueous solubility of organic liquids, *J. Org. Chem.*, 33 (1968), 347-350; C. Hansch, A. Leo, *Exploring QSAR—Fundamentals and Applications in Chemistry and Biology*, American Chemical Society, Washington, 1995; J. Sangster, *Octanol—Water Partition Coefficients: Fundamentals and Physical Chemistry*, Wiley, Chichester, 1997; W. Jorgensen, E. Duffy, *Advanced Drug Delivery Reviews*, (54), 2002, 355-366).

The invention also concerns the compounds of general formula (I') defined above wherein $R_1$ is H, $R_2$ is $OCH_3$, and $R_3$ and $R_4$ simultaneously represent $CH_3$ in the treatment and/or prevention of skin ageing and the treatment and/or prevention of pigmentation disorders.

The invention also concerns the compounds of general formula (I') defined above wherein $R_1$ is H, $R_2$ is $OCH_3$, and $R_3$ and $R_4$ simultaneously represent $CH_3$:
  for depigmentation of the skin and/or head hair and/or body generally when the compound has a value of log P>4;
  or propigmentation of the skin and/or head hair and/or body hair generally when the compound has a value of log P<3.5.

The present invention concerns the said compounds of general formula (I') for cosmetic use thereof as:
  antioxidant active ingredient;
  depigmenting active ingredient generally when the compound has a value of log P>4;
  or propigmenting active ingredient when the compound has a value of log P<3.5.

The present invention concerns a topical composition, characterized in that as active ingredient it contains at least one compound of general formula (I') in association with a pharmaceutically or cosmetically acceptable excipient.

The depigmenting activity which generally consists of reducing and/or inhibiting the production of melanin responsible for pigmentation, or of reducing the transport of melanin into the dendrites, can assume different types of actions in the meaning of the present invention:
  reducing and/or eliminating pigmentation spots such as hyperpigmentation spots due to pro-inflammatory stress (e.g. UV-induced brownish pigment spots) and chloasma,
or:
  whitening and/or lightening the skin and/or body hair and/or head hair, preferably in order to:
    unify the complexion, which is characterized by obtaining a uniform skin complexion, that is lighter, more transparent, more luminous. Skin radiance is therefore improved. The advantages obtained are of particular interest for sensitive skin irrespective of type (dry, normal, greasy) and more particularly for dull skin, lack lustre skin,
and/or:
  treat certain unsightly pigment spots due to epidermal hyperpigmentation, such as cutaneous age spots in particular. The depigmenting activity in the meaning of the present invention then translates as visible attenuation of the intensity and size of pigment spots and/or the prevented onset of additional spots.

The propigmenting activity involves promoting an increase in melanin synthesis in the melanocytes of the epidermis or hair bulb:
  with a view to giving a tanned appearance, or for preparing skin to sun exposure;
  but also for therapeutic purposes to repigment depigmented skin, for example in cases of vitiligo, or to pigment body or head hair, in particular for the treatment and prevention of greying of hair, canities.

The present invention concerns the compounds of general formula (I') wherein $R_1$ is H, $R_2$ is $OCH_3$, and $R_3$ and $R_4$ are simultaneously $CH_3$ for use thereof as antioxidizing active ingredient, depigmenting active ingredient, or propigmenting active ingredient.

The present invention also concerns the topical use of the cosmetic compositions containing a formula (I') compound for the treatment and/or prevention of skin ageing and the treatment and/or prevention of pigmentation disorders.

The invention also concerns the topical use of cosmetic compositions containing an above-defined compound of general formula (I') and which, when they have a value of log P>4, are generally useful for depigmentation of the skin and/or head hair and/or body hair.

The invention also concerns the topical use of cosmetic compositions containing a compound of above-defined general formula (I') which, when they have a value of log P<3.5, are generally useful for propigmentation of the skin and/or head hair and/or body hair.

The compounds of general formula (I') can be chosen from among the list of following compounds:

10-dodecyl-9-(4-hydroxy-3-methoxyphenyl)-3,3,6,6-tetramethyl-3,4,6,7,9,10-hexahydroacridine-1,8(2H,5H)-dione (Example 1);

10-decyl-9-(3,4-dihydroxyphenyl)-3,3,6,6-tetramethyl-3,4,6,7,9,10-hexahydroacridine-1,8(2H,5H)-dione (Example 3);

9-(3,4-dihydroxyphenyl)-10-methyl-3,6-diphenyl-3,4,6,7,9,10-hexahydroacridine-1,8(2H,5H)-dione (Example 5);

10-dEcyl-9-(3,4-dihydroxyphenyl)-3,6-diphenyl-3,4,6,7,9,10-hexahydroacridine-1,8(2H,5H)-dione (Example 6);

10-decyl-9-(4-hydroxy-3,5-dimethoxyphenyl)-3,3,6,6-tetramethyl-3,4,6,7,9,10-hexahydroacridine-1,8(2H,5H)-dione (Example 7);

10-dodecyl-9-(3,5-di-tert-butyl-4-hydroxyphenyl)-3,3,6,6-tetramethyl-3,4,6,7,9,10-hexahydroacridine-1,8(2H,5H)-dione (Example 8);

10-dodecyl-9-(4-hydroxy-3-methoxyphenyl)-3,6-diisopropyl-3,4,6,7,9,10-hexahydroacridine-1,8(2H,5H)-dione (Example 9);

10-butyl-9-(4-hydroxy-3-methoxyphenyl)-3,3,6,6-tetramethyl-3,4,6,7,9,10-hexahydroacridine-1,8(2H,5H)-dione (Example 14);

9-(4-hydroxy-3-methoxyphenyl)-3,3,6,6-tetramethyl-10-pentyl-3,4,6,7,9,10-hexahydroacridine-1,8(2H,5H)-dione (Example 15);

10-hexyl-9-(4-hydroxy-3-methoxyphenyl)-3,3,6,6-tetramethyl-3,4,6,7,9,10-hexahydroacridine-1,8(2H,5H)-dione (Example 16);

10-heptyl-9-(4-hydroxy-3-methoxyphenyl)-3,3,6,6-tetramethyl-3,4,6,7,9,10-hexahydroacridine-1,8(2H,5H)-dione (Example 17);

9-(4-hydroxy-3-methoxyphenyl)-3,3,6,6-tetramethyl-10-octyl-3,4,6,7,9,10-hexahydroacridine-1,8(2H,5H)-dione (Example 18);

9-(4-hydroxy-3-methoxyphenyl)-3,3,6,6-tetramethyl-10-nonyl-3,4,6,7,9,10-hexahydroacridine-1,8(2H,5H)-dione (Example 19);

9-(4-hydroxy-3-methoxyphenyl)-3,3,6,6-tetramethyl-10-undecyl-3,4,6,7,9,10-hexahydroacridine-1,8(2H,5H)-dione (Example 20);

10-benzyl-9-(4-hydroxy-3-methoxyphenyl)-3,3,6,6-tetramethyl-3,4,6,7,9,10-hexahydroacridine-1,8(2H,5H)-dione (Example 21);

9-(4-hydroxy-3-methoxyphenyl)-3,3,6,6-tetramethyl-10-(3-phenylpropyl)-3,4,6,7,9,10-hexahydroacridine-1,8(2H,5H)-dione (Example 23);

10-(2,2-diphenylethyl)-9-(4-hydroxy-3-methoxyphenyl)-3,3,6,6-tetramethyl-3,4,6,7,9,10-hexahydroacridine-1,8(2H,5H)-dione (Example 24); and:

9-(3,4-dihydroxyphenyl)-3,3,6,6-tetramethyl-3,4,6,7,9,10-hexahydroacridine-1,8(2H,5H)-dione (Example 2);

9-(3,4-dihydroxyphenyl)-3,3,6,6,10-pentamethyl-3,4,6,7,9,10-hexahydroacridine-1,8(2H,5H)-dione (Example 4);

9-(4-hydroxy-3-methoxyphenyl)-3,3,6,6-tetramethyl-3,4,6,7,9,10-hexahydroacridine-1,8(2H,5H)-dione (Example 10);

9-(4-hydroxy-3-methoxyphenyl)-3,3,6,6,10-pentamethyl-3,4,6,7,9,10-hexahydroacridine-1,8(2H,5H)-dione (Example 11);

10-ethyl-9-(4-hydroxy-3-methoxyphenyl)-3,3,6,6-tetramethyl-3,4,6,7,9,10-hexahydroacridine-1,8(2H,5H)-dione (Example 12);

9-(4-hydroxy-3-methoxyphenyl)-3,3,6,6-tetramethyl-10-propyl-3,4,6,7,9,10-hexahydroacridine-1,8(2H,5H)-dione (Example 13);

9-(4-hydroxy-3-methoxyphenyl)-3,3,6,6-tetramethyl-10-phenethyl-3,4,6,7,9,10-hexahydroacridine-1,8(2H,5H)-dione (Example 22).

The present invention concerns a cosmetic method for treating and/or preventing ageing of the skin comprising the application to the skin of a composition containing at least one compound of general formula (I').

The present invention concerns a method for whitening and/or lightening human skin and/or body hair and/or head hair comprising the application to the skin and/or body hair and/or head hair of a cosmetic composition containing at least one compound of general formula (I') essentially having a value of log P>4.

The present invention concerns a method for giving a tanned appearance to the skin or for preparing skin for sun exposure comprising the application to the skin of a cosmetic composition containing at least one compound of general formula (I') essentially having a value of log P<3.5.

The invention also extends to the method for synthesizing compounds of general formula (I) as illustrated by the synthesis scheme below:

Synthesis scheme

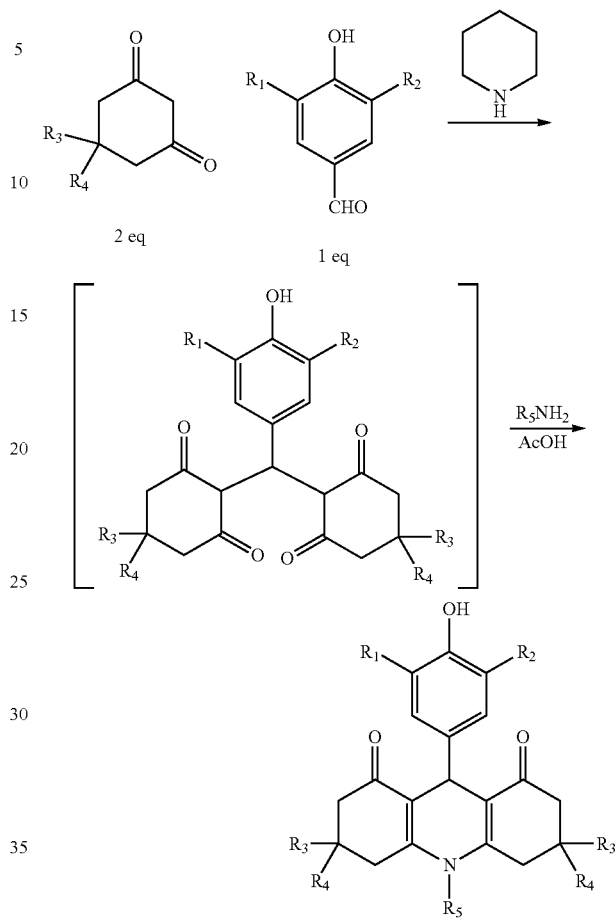

The present invention also concerns a method for preparing compounds of general formulas (I) or (I') such as defined in the foregoing, which involves the reaction of a cyclohexanedione of general formula (II):

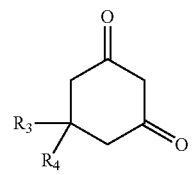

(II)

with a 4-hydroxybenzaldehyde of general formula (III):

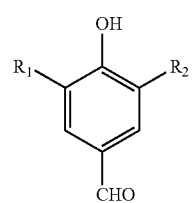

(III)

leading to an intermediate product of formula (IV):

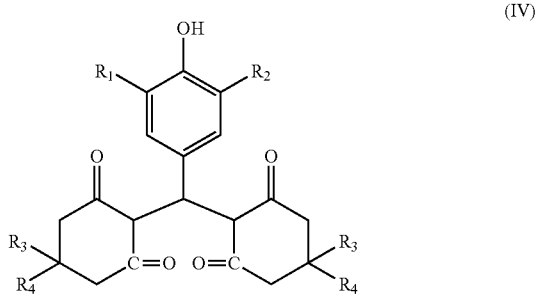

which is caused to react with an alkylamine of formula (V):

$$R_5NH_2 \quad (V)$$

to lead to the corresponding compounds of formula (I), the designations of the radicals $R_1$ to $R_5$ in the different general formulas (II) to (V) being such as previously defined.

According to another characteristic, the present invention concerns a method whereby the reaction between the compounds of general formulas (II) and (III) is conducted in the presence of piperidine.

According to a further characteristic, the invention concerns a method whereby the reaction between the compounds of general formulas (IV) and (V) is conducted in the presence of acetic acid.

Pharmacological Evaluation

A) Assay of Melanin in B16-F10 Cells

Principle

It is a test to measure the synthesis of melanin by colorimetric assay on a murine melanoma cell line: line B16-F10. With this test it is possible to evaluate the depigmenting or propigmenting property of active ingredients.

The B16-F10 cells were seeded in 96-well plates in DMEM medium supplemented with FCS (foetal calf serum), and incubated 24 h at 37° C., 5% $CO_2$. The cells were stimulated with 0.1 μM α-MSH (to stimulate melanin synthesis, the observed stimulation being about 150%) and treated 72 h with the active ingredients to be assayed. Each concentration of active ingredient was assayed at least in triplicate. Total melanin and intracellular melanin dissolved in lysis buffer were assayed by absorbance read-off at 405 nm. The total proteins were assayed in the lysate and the results expressed in mg melanin/mg proteins. Percentage activity was calculated as follows:

$$\% \text{ activity} = \frac{\text{Treated normalised mean} - \text{Reference (MSH) normalised mean}}{\text{Reference (MSH) normalised mean}} \times 100$$

A negative value indicates inhibition of the melanin synthesis and translates depigmenting activity of the compound, whereas a positive value indicates induced melanin synthesis and translates a propigmenting property of the molecule.

Biological Material:
B16-F10 cell lines between P10 and P20 (murine melanocytes) (ATCC, CRL-6475);
reagents:
DMEM without Phenol Red (GIBCOBRL, 118800-028), 200 mM glutamax-I supplement (GIBCOBRL, 35050-038), glucose (SIGMA, G7021), PBS (GIBCOBRL, 14190-094), foetal calf serum (Invitrogen, 10270-098), trypsin-EDTA (GIBCO-BRL, 25300-054), NaOH (Sigma, S8045-500G), DMSO (Sigma, 471267-11), Nle, Phe-Melanocyte Stimulating Hormone (Sigma, M-8764), melanin (Sigma, M-0418), BCA-COPPER (SIGMA, B9643 and C2284), BSA (SIGMA, P0914)

B) Test to Study Anti-Oxidizing Capability Using Chemiluminescence (Photochem Analytic Jena)

Principle

This test is used to determine the anti-oxidizing capability of the molecules. It is a method which generates free radicals via photochemical signal. The intensity of oxidation is 1000 times higher than obtained under normal conditions.

Detection is performed using chemiluminescence. This allows evaluation of water-soluble and liposoluble antioxidant molecules or extracts The results are expressed in equivalent quantity of vitamin C or Trolox (6-hydroxy-2,5,7,8-tetramethylchroman-2-carboxylic acid) respectively. Sensitivity is in the order of one nanomole.

The anti-oxidizing activity studied in this test represents the capability of specifically trapping superoxide anions by chemiluminescence.

The quantified results are expressed in Trolox equivalent (standard) or in "μg of product per 1 μg of Trolox". This means that a quantity x of sample is needed to obtain activity equivalent to the activity detected with 1 μg of standard. It is the antioxidizing power in relation to a reference; this avoids having to take into account the concentrations tested.

Generation of Oxygenated Free Radicals.

The superoxide radical: $O_2^{\circ-}$ is generated by photochemical reaction:

$$L + h\nu(UV) + O_2 \rightarrow L^*O_2 \rightarrow L^{\circ+} + O_2^{\circ-}$$

L*: luminol in the excited state
$L^{\circ+}$: luminol radical

Signal Detection

Part of the superoxide anions are inhibited by the antioxidants. The remaining free radicals are quantified by chemiluminescence.

$$L^{\circ+} + O_2^{\circ-} \rightarrow N2 + AP^{*2-} \rightarrow AP^{2-} + h\nu \text{ (luminescence)}$$

$AP^{*2-}$: aminophthalate in the excited state

| Name | Conditions | Photosensitizing | Antioxidant |
|---|---|---|---|
| Blank | 100% $O_2^{\circ-}$ generated | + | — |
| Standards | standard range: 1 to 3 nmol | + | vitamin C or Trolox |
| Assay | +/- $O_2^{\circ-}$ generated | + | molecule x to be assayed | a) Assay of Melanin in B16-F10 Cells

The results are grouped together in summary Table 2 below.

Interpretation of Results:

A negative value indicates inhibition of melanin synthesis, a positive value stimulation of melanin synthesis.

It was found that:
the tested compounds with log P>4 show good inhibiting capability of melanin synthesis;
the tested compounds with log P<3.5 show good inducing capability of melanin synthesis.

B) Test to Study Antioxidizing Capability by Chemiluminescence (Photochem Analytic Jena)

The results are also grouped together in summary Table 1 below.

The scale for interpretation of results is as follows:
| Products | µg sample per 1 µg of Trolox | Activity |
|---|---|---|
| Vitamin C | 0.1 to 3.0 | very good |
| BHT | 3.01 to 50 | good |
| Cystein | 50.1 to 1000 | average |
| Albumin | >1000 | poor |
| Lipoic acid | NEGATIVE | none |
| Example | Structure of compound | µg sample per 1 µg of Trolox |
|---|---|---|
| Example 1 | 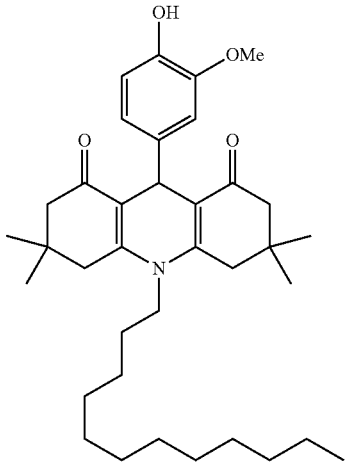 [SMILES: CCCCCCCCCCCCN1C2=C(C(=O)CC(C)(C)C2)C(c2ccc(O)c(OC)c2)C2=C1CC(C)(C)CC2=O] | 2.45 |
| Example 2 | 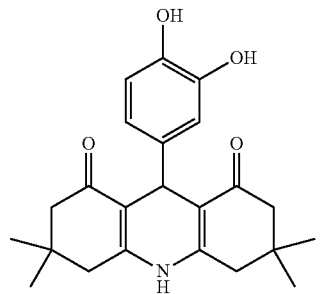 | 0.04 |
| Example 3 | 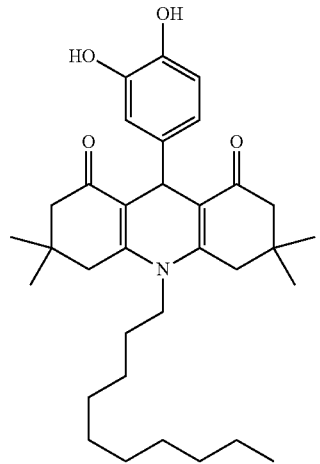 | 0.015 |

-continued

| Example | Structure of compound | μg sample per 1 μg of Trolox |
|---|---|---|
| Example 4 | | 0.017 |
| Example 5 | | 0.05 |
| Example 6 | | 0.04 |
| Example 7 | | 0.81 |

-continued

| Example | Structure of compound | μg sample per 1 μg of Trolox |
|---|---|---|
| Example 8 | [structure: 9-(3,5-di-tert-butyl-4-hydroxyphenyl)-3,3,6,6-tetramethyl-10-dodecyl-octahydroacridine-1,8-dione] | 61.9 |
| Example 9 | [structure: 9-(4-hydroxy-3-methoxyphenyl)-3,6-diisopropyl-10-dodecyl-octahydroacridine-1,8-dione] | 1.57 |

Most of the compounds displayed good anti-oxidizing activity.

Most of the compounds showed results comparable to vitamin C. All the compounds showed results lower than 1000 μg of Trolox (62 μg being the lowest result obtained with Example 8); they therefore all have anti-oxidizing activity of interest.

TABLE 2

| Example | Compound structure | Melanin synthesis on B16 | LogP |
|---|---|---|---|
| Example 3 | [structure: 9-(3,4-dihydroxyphenyl)-3,3,6,6-tetramethyl-10-decyl-octahydroacridine-1,8-dione] | −46% at 20 μM | 5.21 |

TABLE 2-continued
| Example | Compound structure | Melanin synthesis on B16 | LogP |
|---|---|---|---|
| Example 7 | 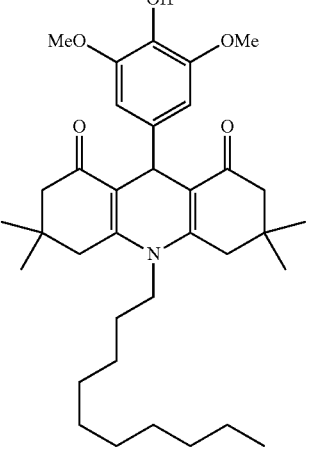 | −56% at 10 μM | 5.34 |
| Example 8 | 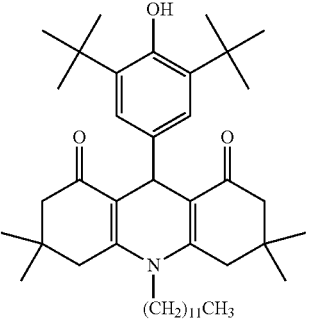 | −46% at 20 μM | >5 |
| Example 9 | 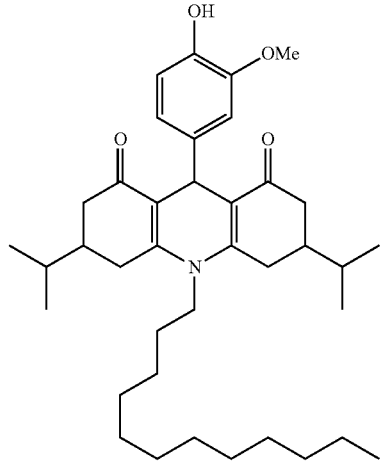 [SMILES: CCCCCCCCCCCCN1C2=C(C(=O)CC(C(C)C)C2)C(c2ccc(O)c(OC)c2)C2=C1CC(C(C)C)CC2=O] | −49% at 10 μM | >5 |
| — | 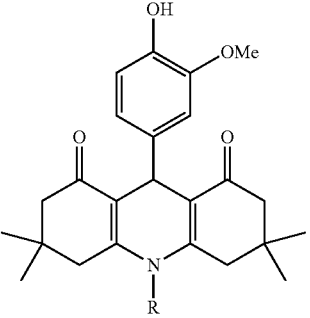 | — | — |

TABLE 2-continued

| Example | Compound structure | Melanin synthesis on B16 | LogP |
|---|---|---|---|
| Example 10 | H | +29% at 100 μM | 1.49 |
| Example 11 | —CH$_3$ | +47% at 100 μM | 1.72 |
| Example 12 | —CH$_2$CH$_3$ | +72% at 50 μM | 2.06 |
| Example 13 | —(CH$_2$)$_2$CH$_3$ | +43% at 50 μM | 2.55 |
| Example 14 | —(CH$_2$)$_3$CH$_3$ | +45% at 20 μM | 2.97 |
| Example 15 | —(CH$_2$)$_4$CH$_3$ | +42% at 50 μM | 3.38 |
| Example 16 | —(CH$_2$)$_5$CH$_3$ | — | 3.8 |
| Example 17 | —(CH$_2$)$_6$CH$_3$ | −68% at 20 μM | 4.22 |
| Example 18 | —(CH$_2$)$_7$CH$_3$ | −59% at 5 μM | 4.63 |
| Example 19 | —(CH$_2$)$_8$CH$_3$ | −42% at 5 μM | 5.05 |
| Example 20 | —(CH$_2$)$_{10}$CH$_3$ | −57% at 5 μM | 5.89 |
| Example 1 | —(CH$_2$)$_{11}$CH$_3$ | −40% at 2 μM | 6.3 |
| Example 21 | —CH$_2$Ph | +48% at 100 μM | 3.46 |
| Example 22 | —(CH$_2$)$_2$Ph | — | 3.74 |
| Example 23 | —(CH$_2$)$_3$Ph | −37% at 10 μM | 4.15 |
| Example 24 | —CH$_2$CH(Ph)$_2$ | −37% at 5 μM | 5.32 |

Recall: A negative value indicates inhibition of melanin synthesis; a positive value indicates stimulation of melanin synthesis.

EXAMPLES OF SYNTHESIS

Example 1

10-dodecyl-9-(4-hydroxy-3-methoxyphenyl)-3,3,6,6-tetramethyl-3,4,6,7,9,10-hexahydroacridine-1,8(2H,5H)-dione

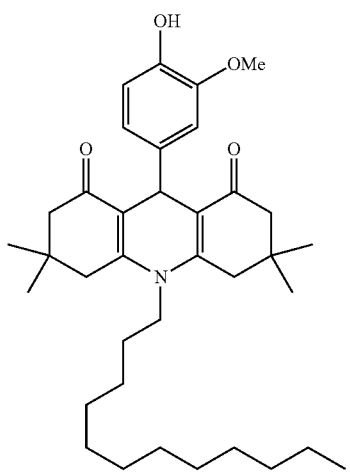 [SMILES: CCCCCCCCCCCCN1C2=C(C(=O)CC(C)(C)C2)C(c2ccc(O)c(OC)c2)C2=C1CC(C)(C)CC2=O]

General Procedure

To a suspension of 2.80 g of 5,5-dimethyl-1,3-cyclohexanedione (dimedone, 20 mmol) and 1.52 g of vanillin (10 mmol) in 40 mL of ethanol were added 49.45 μL of piperidine (0;5 mmol). The mixture was brought under reflux to a temperature of 110° C. and the particles in suspension were seen to solubilize in a clear orange solution. After a reaction time of 4 h the solution was cooled to ambient temperature for 10 min, then placed 10 min in an ice bath; the precipitate obtained was filtered with minimum cold ethanol and n-pentane. The solid was dried in vacuo in an oven at least overnight under 50 mbar and at 40° C. to obtain a white solid with a mean yield of 86%.

To the mixture of 1.24 g of intermediate product (3 mmol) and 0.55 g of n-dodecylamine (3 mmol) were added 5 mL of acetic acid. The mixture was brought under reflux to a temperature of 140° C. and the particles in suspension were seen to solubilize into a clear yellow solution. After a reaction time of 4 h the solution was cooled to ambient temperatures for 10 min and evaporated to dryness. Chromatography was performed using a gradient of 90:10 to 50:50 in heptane/ethyl acetate. The pure fraction was recovered and evaporated. The solid was dried in vacuo in an oven at least overnight under 50 mbar and at 40° C. to obtain a yellow solid with a mean yield of 50%.

$^1$H-NMR (400 MHz, CDCl$_3$, δ): 0.88 (t, 3H), 1.00 (S, 6H), 1.09 (s, 6H), 1.27 (s, 16H), 1.33 (m, 2H), 1.59 (m, 2H), 2.22 (s, 4H), 2.38 (d, cyst. AB, 2H), 2.51 (d, syst. AB, 2H), 3.62 (t, 2H), 3.85 (s, 3H), 5.17 (s, 1H), 5.43 (s, 1H), 6.50 (dd, 1H), 6.67 (d, 1H), 7.01 (s, 1H).

$^{13}$C-NMR (100 MHz, CDCl$_3$, δ): 14.0, 22.6, 26.5, 27.5, 29.2, 29.4, 29.6, 31.5, 31.7, 32.3, 40.4, 44.7, 49.8, 56.1, 104.5, 115.2, 132.8, 137.2, 146.4, 149.6, 195.6.

MS (ESI$^+$): 564.4 [M+H]$^+$.

Rf (cyclohexane/AcOEt; 1:1): 0.31.

Example 2

9-(3,4-dihydroxyphenyl)-3,3,6,6-tetramethyl-3,4,6,7,9,10-hexahydroacridine-1,8(2H,5H)-dione

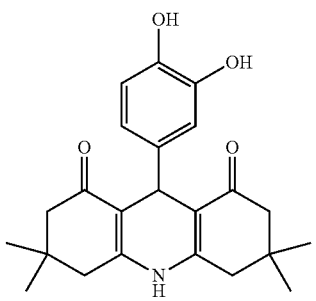

$^1$H-NMR (400 MHz, DMSO-d6, δ): 0.88 (s, 6H), 1.00 (s, 6H), 2.00-2.40 (m, 8H), 4.64 (s, 1H), 6.38 (s, 1H), 6.47 (s, 1H), 6.59 (s, 1H), 8.51 (s, 2H, OH), 9.17 (s, 1H, NH).

¹³C-NMR (100 MHz, DMSO d6, δ): 26.4, 29.0, 31.6, 32.0, 40.0, 50.3, 111.8, 114.6, 115.4, 118.6, 138.4, 142.8, 144.1, 148.6, 194.2.

MS (APCI⁺): 282.2 [M+H]⁺

Example 3

10-decyl-9-(3,4-dihydroxyphenyl)-3,3,6,6-tetramethyl-3,4,6,7,9,10-hexahydroacridine-1,8(2H,5H)-dione

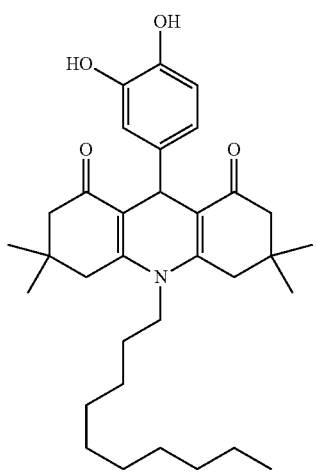

¹H-NMR (400 MHz, DMSO-d6, δ): 0.85 (t, 3H), 0.92 (s, 6H), 1.01 (s, 6H), 1.23 (s, XH), 1.49 (m, 2H), 2.08 (dd, 4H), 2.60 (dd, 4H), 3.67 (t, 2H), 4.64 (s, 1H), 6.26 (s, 1H), 6.44 (s, 1H), 6.58 (s, 1H), 8.42 (s, 1H, OH), 8.51 (s, 1H, OH).

¹³C-NMR (100 MHz, DMSO-d6, δ): 13.8, 21.9, 25.6, 26.9, 28.6, 29.5, 30.5, 31.1, 31.9, 40.0, 44.1, 49.5, 113.7, 114.6, 115.1, 117.1, 137.2, 142.8, 144.2, 150.9, 194.9.

MS (ESI⁺): 522.3 [M+H]⁺.

Rf (cyclohexane/EtOAc; 1:1): 0.16.

Example 4

9-(3,4-dihydroxyphenyl)-3,3,6,6,10-pentamethyl-3,4,6,7,9,10-hexahydroacridine-1,8(2H,5H)-dione

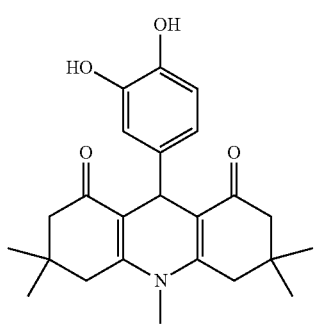

¹H-NMR (400 MHz, DMSO-d6, δ): 0.96 (s, 6H), 0.99 (s, 6H), 2.11 (dd, 4H), 2.40 (d, syst. AB, 2H), 2.74 (d, syst. AB, 2H), 3.24 (s, 3H), 4.86 (s, 1H), 6.28 (d, 1H, 6.46 (d, 1H), 6.54 (s, 1H), 8.42 (s, 1H, OH), 8.52 (s, 1H, OH).

¹³C-NMR (100 MHz, DMSO-d6, δ): 26.2, 27.7, 27.9, 28.2, 29.5, 32.0, 33.1, 40.0, 49.5, 113.1, 114.8, 114.9, 117.3, 137.1, 142.9, 144.2, 152.0, 194.6.

MS (ESI⁺): 396.2 [M+H]⁺.

Rf (CHCl₃/MeOH; 95:5): 0.26.

Example 5

9-(3,4-dihydroxyphenyl)-10-methyl-3,6-diphenyl-3,4,6,7,9,10-hexahydroacridine-1,8(2H,5H)-dione

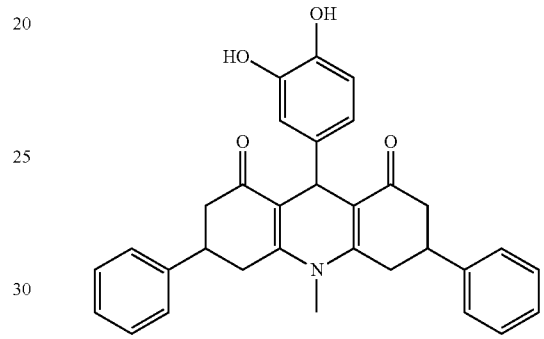

MS (ESI⁺): 492.2 [M+H]⁺.

Rf (EtOAc): 0.76.

Example 6

10-decyl-9-(3,4-dihydroxyphenyl)-3,6-diphenyl-3,4,6,7,9,10-hexahydroacridine-1,8(2H,5H)-dione

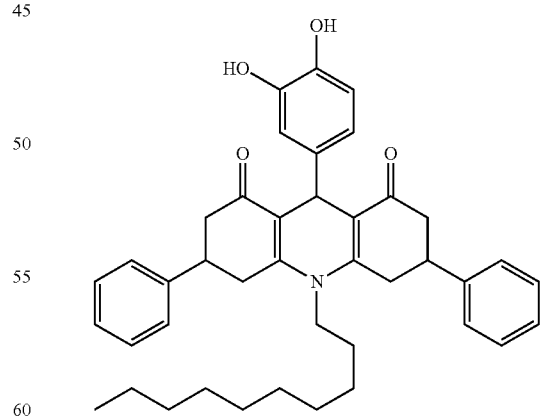

¹H-NMR (400 MHz, CDCl₃, δ): 0.87 (t, 3H), 1.21 (s, 14H), 1.58 (m, 2H), 1.70 (m, 2H), 2.54-3.02 (m, 8H), 3.24-3.63 (m, 4H), 5.26 (s, 1H), 6.56 (m, 2H), 6.95 (d, 1H), 7.28 (m, 10H).

MS (ESI⁺): 618.3 [M+H]⁺.

Example 7

10-decyl-9-(4-hydroxy-3,5-dimethoxyphenyl)-3,3,6,6-tetramethyl-3,4,6,7,9,10-hexahydroacridine-1,8(2H,5H)-dione

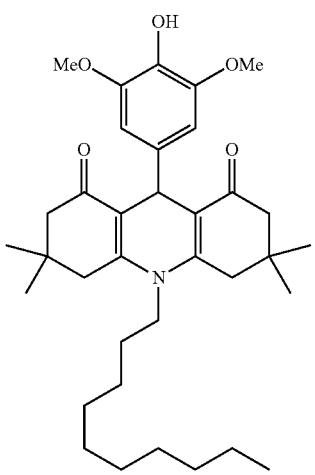

$^1$H-NMR (400 MHz, CDCl$_3$, δ): 0.88 (t, 3H), 1.02 (s, 6H), 1.10 (s, 6H), 1.27 (s, 12H), 1.31 (m, 2H), 1.59 (m, 2H), 2.23 (s, 4H), 2.40 (d, syst. AB, 2H), 2.50 (d, syst. AB, 2H), 3.62 (t, 2H), 3.80 (s, 6H), 5.20 (s, 1H), 6.52 (s, 2H).
$^{13}$C-NMR (100 MHz, CDCl$_3$, δ): 14.0, 22.6, 26.5, 27.5, 29.2, 29.4, 29.6, 31.5, 31.7, 32.3, 40.4, 44.7, 49.8, 56.1, 104.5, 115.2, 132.8, 137.2, 146.4, 149.6, 195.6.
MS (ESI$^+$): 566.4 [M+H]$^+$.
Rf (cyclohexane/AcOEt; 1:1): 0.18.

Example 8

10-dodecyl-9-(3,5-di-tert-butyl-4-hydroxyphenyl)-3,3,6,6-tetramethyl-3,4,6,7,9,10-hexahydroacridine-1,8(2H,5H)-dione

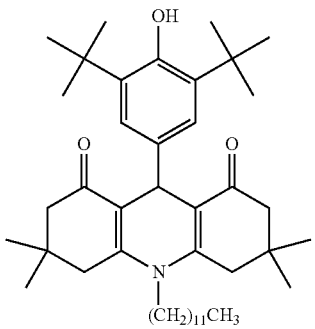

$^1$H-NMR (400 MHz, CDCl$_3$, δ): 0.88 (t, 3H), 1.02 (s, 6H), 1.09 (s, 6H), 1.26 (s, 18H), 1.35 (s, 18H), 1.56 (m, 2H), 2.22 (m, 4H), 2.46 (m, 4H), 3.56 (t, 2H), 4.91 (s, 1H), 5.20 (s, 1H), 7.00 (s, 2H).
$^{13}$C-NMR (100 MHz, CDCl$_3$, δ): 26.53, 26.87, 27.59, 29.15, 29.29, 29.41, 29.50, 29.57, 30.43, 30.93, 31.86, 32.44, 34.17, 40.48, 44.89, 50.00, 115.57, 124.06, 134.36, 136.36, 149.69, 151.69, 195.65.

MS (ESI$^+$): 646.5 [M+H]$^+$.
Rf (cyclohexane/EtOAc; 7:3): 0.13.

Example 9

10-dodecyl-9-(4-hydroxy-3-methoxyphenyl)-3,6-diisopropyl-3,4,6,7,9,10-hexahydroacridine-1,8(2H,5H)-dione

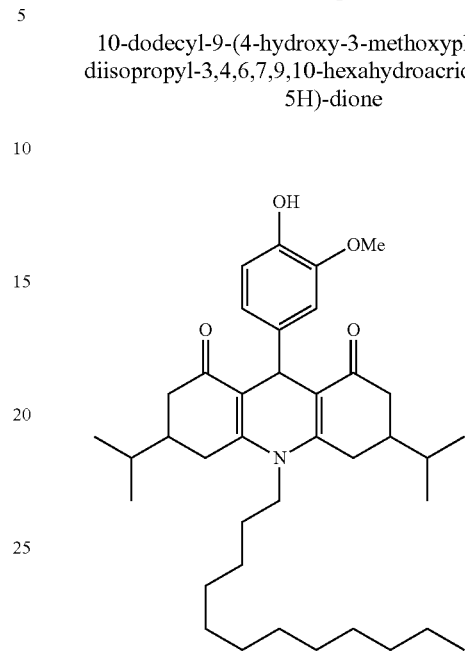

$^1$H-NMR (400 MHz, CDCl$_3$, δ): 0.86-0.96 (m, 15H), 1.26 (m, 19H), 1.60-2.47 (m, 13H), 2.52 (m, 1H), 2.56 (m, 1H), 3.66 (m, 2H), 3.87 (s, 3H), 5.18 (s, 1H), 5.47 (s, 1H), 6.44 (dd, 1H), 6.67 (d, 1H), 7.07 (d, 1H).
MS (ESI$^+$): 592.4 [M+H]$^+$.
Rf (cyclohexane/EtOAc; 1:1): 0.46.

Example 10

9-(4-hydroxy-3-methoxyphenyl)-3,3,6,6-tetramethyl-3,4,6,7,9,10-hexahydroacridine-1,8(2H,5H)-dione

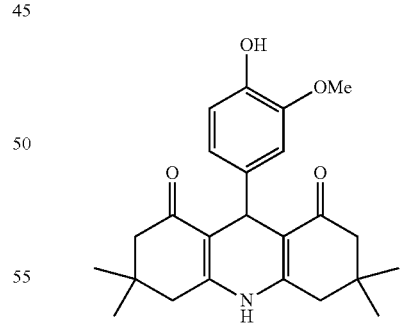

$^1$H-NMR (300 MHz, DMSO-d6, δ): 0.80 (s, 6H), 1.01 (s, 6H), 2.00-2.40 (m, 8H), 3.65 (s, 3H), 4.72 (s, 1H), 6.50 (2d, 2H), 6.70 (s, 1H), 8.58 (s, 1H, OH), 9.23 (s, 1H, NH).
$^{13}$C-NMR (75 MHz, DMSO-d6, δ): 26.74, 29.53, 32.24, 32.74, 50.68, 55.85, 112.11, 112.58, 115.11, 120.13, 138.86, 144.69, 147.05, 149.32, 194.80.
MS (ES$^+$): 418.2 [M+Na]$^+$; 813.5 [2M+Na]$^+$.
MS (ES$^-$): 394.2 [M–H]$^-$.
Mp=309.8° C.

Example 11

9-(4-hydroxy-3-methoxyphenyl)-3,3,6,6,10-pentamethyl-3,4,6,7,9,10-hexahydroacridine-1,8(2H,5H)-dione

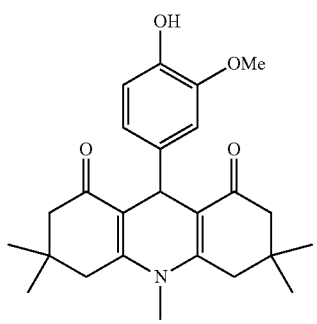

$^1$H-NMR (400 MHz, CDCl$_3$, δ): 1.03 (s, 6H), 1.07 (s, 6H), 2.22 (s, 4H), 2.40 (m, 4H), 3.25 (s, 3H), 3.84 (s, 3H), 5.17 (s, 1H), 5.29 (s, 1H), 6.45 (dd, 1H), 6.67 (d, 1H), 7.02 (d, 1H).

$^{13}$C-NMR (100 MHz, CDCl$_3$, δ): 28.59, 28.64, 31.16, 32.63, 33.41, 40.50, 49.83, 55.79, 111.59, 113.70, 115.10, 118.72, 137.95, 143.62, 145.90, 151.00, 195.55.

MS (ESI$^+$): 410.2 [M+H]$^+$.

Rf (DCM/MeOH; 95:5): 0.33.

Example 12

10-ethyl-9-(4-hydroxy-3-methoxyphenyl)-3,3,6,6-tetramethyl-3,4,6,7,9,10-hexahydroacridine-1,8(2H,5H)-dione

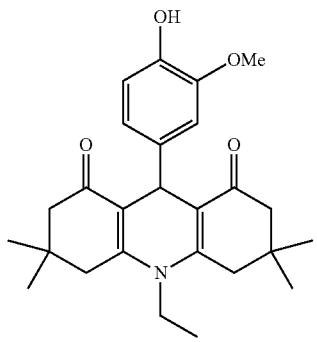

$^1$H-NMR (300 MHz, DMSO-d6, δ): 0.91 (S, 6H), 1.03 (s, 6H), 1.18 (t, 3H), 2.07 (d, 2H), 2.17 (d, 2H), 2.46 (d, 2H), 2.69 (d, 2H), 3.63 (s, 3H), 3.78 (q, 2H), 4.91 (s, 1H), 6.50 (2d, 2H), 6.60 (s, 1H), 8.59 (s, 1H, OH).

$^{13}$C-NMR (75 MHz, DMSO-d6, δ): 16.55, 27.05, 29.37, 30.51, 32.38, 49.91, 55.69, 111.60, 114.06, 115.09, 119.84, 137.87, 144.69, 147.24, 151.22, 195.39.

MS (ES$^+$): 446.1 [M+Na]$^+$; 869.4 [2M+Na]$^+$.

MS (ES$^-$): 422.3 [M−H]$^-$.

Example 13

9-(4-hydroxy-3-methoxyphenyl)-3,3,6,6-tetramethyl-10-propyl-3,4,6,7,9,10-hexahydroacridine-1,8 (2H,5H)-dione

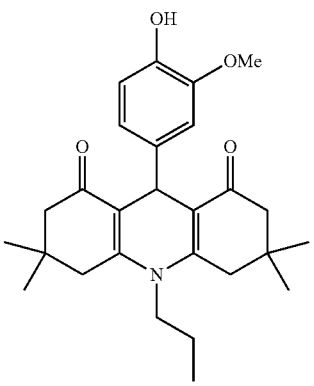

$^1$H-NMR (300 MHz, DMSO-d6, δ): 0.85 (t, 3H), 0.92 (s, 6H), 1.03 (s, 6H), 1.52 (m, 2H), 2.08 (d, 2H, syst. AB), 2.19 (d, 2H, syst. AB), 2.44 (d, 2H, syst. AB), 2.67 (d, 2H, syst. AB), 3.63 (s, 3H), 3.68 (t, 2H), 4.95 (s, 1H), 6.51 (2d, 2H), 6.60 (s, 1H), 8.59 (s, 1H, OH).

$^{13}$C-NMR (75 MHz, DMSO-d6, δ): 11.00, 24.52, 27.09, 29.41, 30.19, 32.21, 32.38, 46.01, 49.93, 55.67, 111.58, 113.89, 115.11, 119.72, 137.59, 144.68, 147.23, 151.52, 195.51.

MS (ES$^+$): 460.1 [M+Na]$^+$; 897.7 [2M+Na]$^+$.

Mp: 259.5° C.

Example 14

10-butyl-9-(4-hydroxy-3-methoxyphenyl)-3,3,6,6-tetramethyl-3,4,6,7,9,10-hexahydroacridine-1,8(2H, 5H)-dione

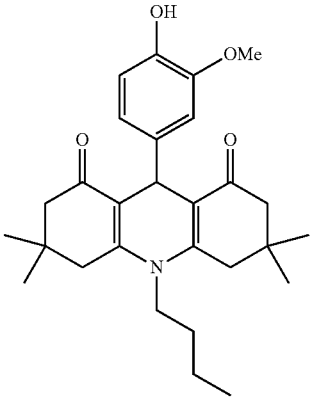

$^1$H-NMR (400 MHz, CDCl$_3$, δ): 1.00 (m, 12H), 1.09 (s, 3H), 1.40 (m, 2H), 1.60 (m, 3H), 2.22 (s, 4H), 2.47 (m, 4H), 3.63 (t, 2H), 3.85 (s, 3H), 5.17 (s, 1H), 5.45 (s, 1H), 6.50 (2d, 1H), 6.68 (d, 1H), 7.02 (d, 1H).

$^{13}$C-NMR (100 MHz, CDCl$_3$, δ): 13.79, 19.86, 27.86, 29.33, 31.35, 32.50, 33.55, 40.43, 44.56, 49.91, 55.79, 111.55, 113.55, 115.57, 119.03, 138.20, 143.55, 145.87, 149.89, 195.73.

MS (ESI⁺): 452.3 [M+H]⁺.
Rf (DCM/MeOH; 98:2): 0.50.

Example 15

9-(4-hydroxy-3-methoxyphenyl)-3,3,6,6-tetramethyl-10-pentyl-3,4,6,7,9,10-hexahydroacridine-1,8(2H,5H)-dione

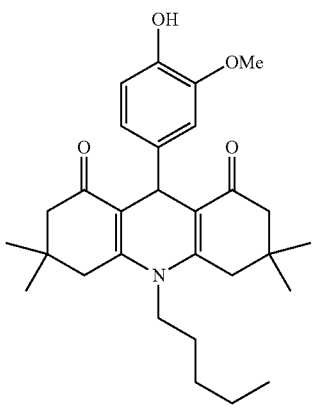

$^1$H-NMR (300 MHz, CDCl$_3$, δ): 0.90 (t, 3H), 1.00 (s, 6H), 1.09 (s, 6H), 1.30 (m, 4H), 1.62 (m, 2H), 2.24 (s, 4H), 2.39 (d, syst. AB, 2H), 2.53 (d, syst. AB, 2H), 3.64 (t, 2H), 3.87 (s, 3H), 5.19 (s, 1H), 5.47 (s 1, 1H), 6.52 (dd, 1H), 6.68 (d, 1H), 7.03 (d, 1H).
$^{13}$C-NMR (75 MHz, CDCl$_3$, δ): 14.3, 22.80, 28.24, 29.14, 29.78, 31.61, 31.75, 32.67, 32.91, 40.85, 45.18, 50.35, 56.21, 111.97, 113.96, 115.98, 119.44, 138.63, 143.98, 146.30, 150.31, 196.12.
MS (ES⁺): 466.2 [M+H]⁺; 953.6 [2M+Na]⁺.
Mp: 194.5° C.

Example 16

10-hexyl-9-(4-hydroxy-3-methoxyphenyl)-3,3,6,6-tetramethyl-3,4,6,7,9,10-hexahydroacridine-1,8(2H,5H)-dione

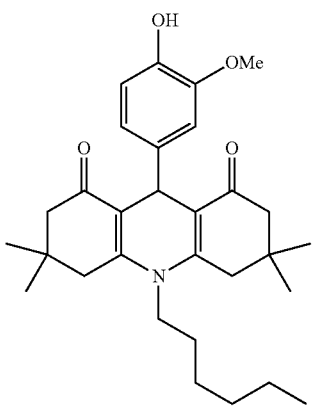

$^1$H-NMR (300 MHz, CDCl$_3$, δ): 0.90 (t, 3H), 1.02 (s, 6H), 1.09 (s, 6H), 1.30 (m, 6H), 1.62 (m, 2H), 2.24 (s, 4H), 2.38 (d, syst. AB, 2H), 2.53 (d, syst. AB, 2H), 3.64 (t, 2H), 3.87 (s, 3H), 5.18 (s, 1H), 5.47 (s 1, 1H), 6.52 (dd, 1H), 6.69 (d, 1H), 7.03 (d, 1H).

$^{13}$C-NMR (75 MHz, DMSO-d6, δ): 16.55, 27.05, 29.37, 30.51, 32.38, 40.91, 55.69, 111.60, 114.06, 115.09, 119.84, 137.87, 144.68, 147.24, 151.22, 195.39.
MS (ES⁺): 480.2 [M+Na]⁺; 981.7 [2M+Na]⁺.
Mp: 177.7° C.

Example 17

10-heptyl-9-(4-hydroxy-3-methoxyphenyl)-3,3,6,6-tetramethyl-3,4,6,7,9,10-hexahydroacridine-1,8(2H,5H)-dione

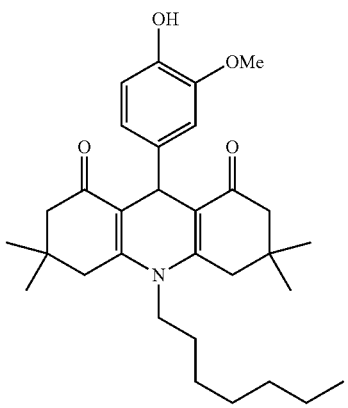 [SMILES: CCCCCCCN1C2=C(C(=O)CC(C)(C)C2)C(c2ccc(O)c(OC)c2)C2=C1CC(C)(C)CC2=O]

$^1$H-NMR (300 MHz, CDCl$_3$, δ): 0.92 (t, 3H), 1.02 (s, 6H), 1.10 (s, 6H), 1.30 (m, 8H), 1.61 (m, 2H), 2.24 (s, 4H), 2.39 (d, syst. AB, 2H), 2.53 (d, syst. AB, 2H), 3.63 (t, 2H), 3.87 (s, 3H), 5.18 (s, 1H), 5.46 (s 1, 1H), 6.52 (dd, 1H), 6.69 (d, 1H), 7.03 (d, 1H).
$^{13}$C-NMR (75 MHz, CDCl$_3$, δ): 14.45, 22.95, 27.01, 28.23, 29.34, 29.79, 31.77, 31.89, 32.06, 40.85, 45.21, 50.35, 56.21, 111.97, 113.96, 115.98, 119.44, 138.64, 143.98, 146.29, 150.29, 196.11.
MS (ES⁺): 494.2 [M+H]⁺; 1009.7 [2M+Na]⁺.
Mp: 154.8° C.

Example 18

9-(4-hydroxy-3-methoxyphenyl)-3,3,6,6-tetramethyl-10-octyl-3,4,6,7,9,10-hexahydroacridine-1,8(2H,5H)-dione

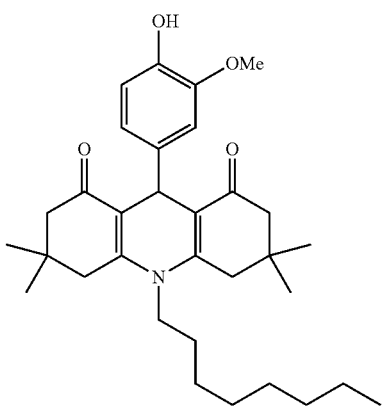 [SMILES: CCCCCCCCN1C2=C(C(=O)CC(C)(C)C2)C(c2ccc(O)c(OC)c2)C2=C1CC(C)(C)CC2=O]

$^1$H-NMR (300 MHz, CDCl$_3$, δ): 0.91 (t, 3H), 1.02 (s, 6H), 1.11 (s, 6H), 1.30 (m, 10H), 1.61 (m, 2H), 2.24 (s, 4H), 2.39 (d, syst. AB, 2H), 2.53 (d, syst. AB, 2H), 3.63 (t, 2H), 3.87 (s, 3H), 5.18 (s, 1H), 5.46 (s 1, 1H), 6.52 (dd, 1H), 6.69 (d, 1H), 7.03 (d, 1H).

¹³C NMR (75 MHz, CDCl₃): δ: 14.47; 23.02; 27.04; 28.23; 29.53; 29.63; 29.79; 31.77; 31.87; 32.11; 32.90; 40.85; 45.21; 50.35; 56.21; 111.97; 113.97; 115.98; 119.44; 138.63; 143.98; 146.29; 150.28; 196.12.
MS (ES⁺): 508.2 [M+H]⁺; 1037.8 [2M+Na]⁺.
Mp: 154.2° C.

Example 19

9-(4-hydroxy-3-methoxyphenyl)-3,3,6,6-tetramethyl-10-nonyl-3,4,6,7,9,10-hexahydroacridine-1,8(2H,5H)-dione

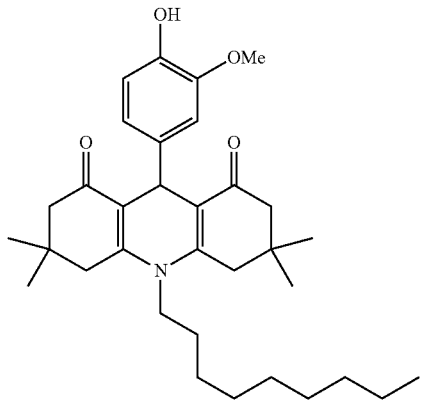 [SMILES: CCCCCCCCCN1C2=C(C(=O)CC(C)(C)C2)C(c2ccc(O)c(OC)c2)C2=C1CC(C)(C)CC2=O]

¹H-NMR (300 MHz, CDCl₃, δ): 0.91 (t, 3H), 1.02 (s, 6H), 1.11 (s, 6H), 1.30 (m, 12H), 1.63 (m, 2H), 2.24 (s, 4H), 2.39 (d, syst. AB, 2H), 2.53 (d, syst. AB, 2H), 3.63 (t, 2H), 3.87 (s, 3H), 5.19 (s, 1H), 5.43 (s 1, 1H), 6.52 (dd, 1H), 6.69 (d, 1H), 7.03 (d, 1H).
¹³C-NMR (75 MHz, CDCl₃, δ): 14.47, 23.03, 27.03, 28.23, 29.58, 29.67, 29.79, 29.83, 31.77, 31.88, 32.22, 32.67, 40.85, 45.21, 50.35, 56.20, 111.96, 113.98, 115.97, 119.45, 138.63, 143.99, 146.30, 150.28, 196.11.
MS (ES⁺): 522.2 [M+H]⁺; 1065.8 [2M+Na]⁺.
Mp: 127.0° C.

Example 20

9-(4-hydroxy-3-methoxyphenyl)-3,3,6,6-tetramethyl-10-undecyl-3,4,6,7,9,10-hexahydroacridine-1,8(2H,5H)-dione

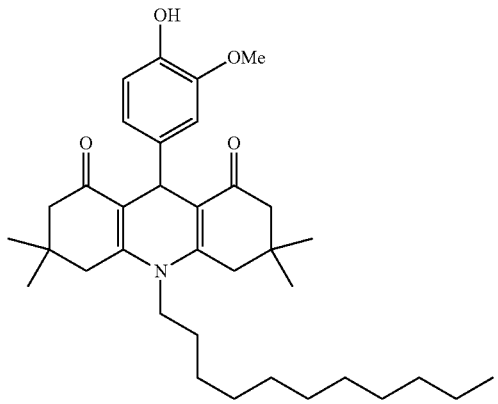 [SMILES: CCCCCCCCCCCN1C2=C(C(=O)CC(C)(C)C2)C(c2ccc(O)c(OC)c2)C2=C1CC(C)(C)CC2=O]

¹H-NMR (300 MHz, CDCl₃, δ): 0.90 (t, 3H), 1.02 (s, 6H), 1.10 (s, 6H), 1.32 (m, 16H), 1.61 (m, 2H), 2.24 (s, 4H), 2.39 (d, syst. AB, 2H), 2.53 (d, syst. AB, 2H), 3.63 (t, 2H), 3.87 (s, 3H), 5.18 (s, 1H), 5.45 (s 1, 1H), 6.52 (dd, 1H), 6.69 (d, 1H), 7.03 (d, 1H).

¹³C-NMR (75 MHz, CDCl₃, δ): 14.50, 23.06, 27.04, 28.23, 29.67, 29.70, 29.79, 29.89, 29.93, 29.98, 31.77, 31.87, 32.27, 32.90, 40.85, 45.21, 50.34, 56.21, 111.96, 113.97, 115.98, 119.44, 138.63, 143.98, 146.29, 150.28, 196.11.
MS (ES⁺): 550.3 [M+H]⁺; 572.2 [M+Na]⁺.
Mp: 118.9° C.

Example 21

10-benzyl-9-(4-hydroxy-3-methoxyphenyl)-3,3,6,6-tetramethyl-3,4,6,7,9,10-hexahydroacridine-1,8(2H,5H)-dione

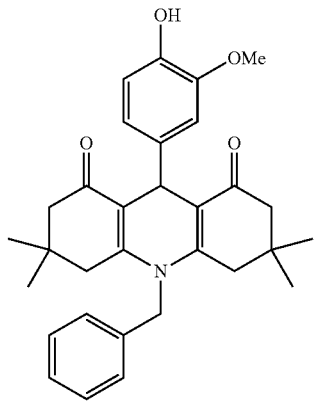

¹H-NMR (400 MHz, CDCl₃, δ): 0.89 (s, 6H), 0.99 (s, 6H), 2.20 (s, 4H), 2.39 (m, 4H), 3.85 (s, 3H), 4.89 (s, 2H), 5.24 (s, 1H), 6.56 (d, 1H), 6.71 (d, 1H), 7.07 (s, 1H), 7.16 (d, 2H), 7.39 (m, 3H).
¹³C-NMR (100 MHz, CDCl₃, δ): 28.04, 28.59, 31.63, 32.66, 40.22, 48.70, 49.95, 50.74, 55.82, 111.85, 113.61, 115.40, 119.39, 125.33, 127.87, 127.96, 129.20, 137.01, 138.26, 143.66, 145.88, 150.34, 195.84.
MS (ESI⁺): 486.2 [M+H]⁺.
Rf (cyclohexane/EtOAc; 1:1): 0.46.

Example 22

9-(4-hydroxy-3-methoxyphenyl)-3,3,6,6-tetramethyl-10-phenethyl-3,4,6,7,9,10-hexahydroacridine-1,8(2H,5H)-dione

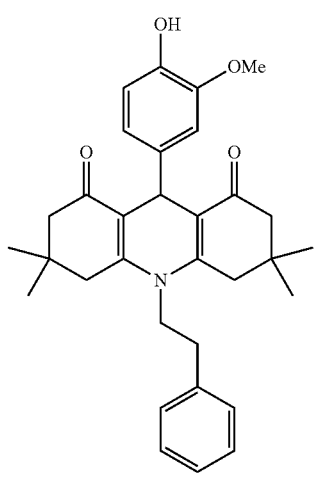

$^1$H-NMR (300 MHz, CDCl$_3$, δ): 0.89 (s, 6H), 1.10 (s, 6H), 2.24 (s, 4H), 2.45 (m, 4H, syst. AB), 2.89 (dd, 2H), 3.88 (s, 3H), 3.91 (dd, 2H), 5.21 (s, 1H), 5.49 (s, 1H), 6.56 (dd, 1H), 6.72 (dd, 1H), 7.07 (d, 1H), 7.17 (dd, 2H), 7.35 (m, 3H).

$^{13}$C-NMR (75 MHz, CDCl$_3$, δ): 27.68, 28.08, 29.97, 31.77, 32.79, 38.22, 41.01, 46.57, 50.30, 56.25, 112.12, 113.98, 116.12, 119.48, 127.68, 129.01, 129.26, 129.43, 137.38, 138.58, 144.06, 146.34, 149.95, 196.16.

MS (ES$^+$): 500.2 [M+H]$^+$; 1021.8 [2M+Na]$^+$.

Example 23

9-(4-hydroxy-3-methoxyphenyl)-3,3,6,6-tetramethyl-10-(3-phenylpropyl)-3,4,6,7,9,10-hexahydroacridine-1,8(2H,5H)-dione

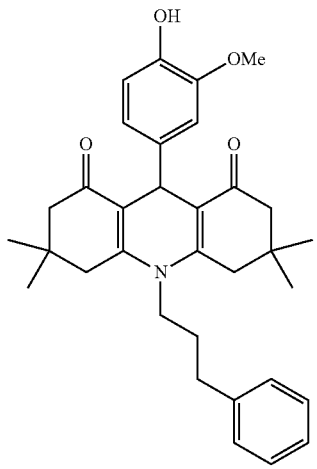

$^1$H-NMR (300 MHz, CDCl$_3$, δ): 0.89 (s, 6H), 1.02 (s, 6H), 1.93 (m, 2H), 2.26 (s, 4H), 2.33 (m, 4H, syst. AB), 2.71 (dd, 2H), 3.61 (m, 2H), 3.84 (s, 3H), 5.15 (s, 1H), 5.47 (s large, 1H), 6.53 (dd, 1H), 6.70 (dd, 1H), 7.01 (d, 1H), 7.20 (dd, 2H), 7.35 (m, 3H).

$^{13}$C-NMR (75 MHz, CDCl$_3$, δ): 28.01, 29.79, 31.84, 32.74, 32.98, 33.06, 40.56, 44.08, 50.30, 56.19, 111.99, 114.06, 116.01, 119.45, 127.07, 128.84, 129.20, 138.72, 140.49, 143.98, 146.28, 150.08, 196.08.

MS (ES$^+$): 514.3 [M+H]$^+$; 1049.9 [2M+Na]$^+$.

Example 24

10-(2,2-diphenylethyl)-9-(4-hydroxy-3-methoxyphenyl)-3,3,6,6-tetramethyl-3,4,6,7,9,10-hexahydroacridine-1,8(2H,5H)-dione

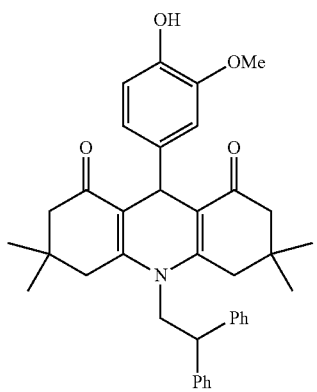

$^1$H-NMR (300 MHz, CDCl$_3$, δ): 0.81 (s, 6H), 1.01 (s, 6H), 2.19 (s, 4H), 2.27 (m, 4H, syst. AB), 3.88 (s, 3H), 3.92 (t, 1H), 4.36 (d, 2H), 5.24 (s, 1H), 5.53 (s 1, 1H), 6.43 (dd, 1H), 6.78 (dd, 1H), 7.03 (d, 1H), 7.17-7.35 (m, 10H).

$^{13}$C-NMR (75 MHz, CDCl$_3$, δ): 27.29, 30.49, 31.22, 32.40, 41.17, 50.25, 50.29, 54.26, 56.25, 112.18, 113.80, 115.61, 119.44, 127.79, 128.31, 129.40, 138.26, 141.63, 144.01, 146.34, 150.59, 196.39.

MS (ES$^+$): 576.2 [M+H]$^+$; 1151.7 [2M+H]$^+$.

The topical composition of the invention is characterized in that the quantity of formula (I') compound varies between 0.01% and 10% by weight and preferably between 0.1% and 5% by weight relative to the total weight of the composition.

The invention claimed is:

1. A method of modifying pigmentation of skin which comprises topically administering a composition containing at least one compound of general formula (I')

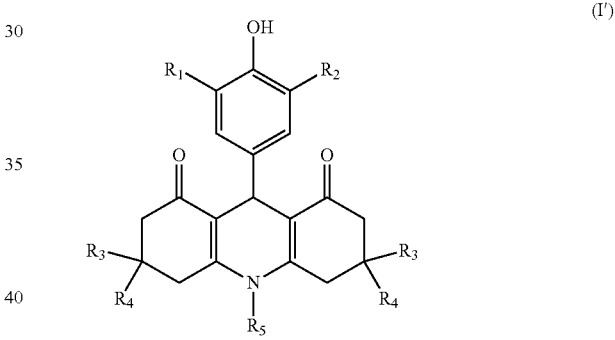

(I')

where:

R$_1$ and R$_2$ are simultaneously or independently H, OH, OCH$_3$ or a C$_1$-C$_5$ alkyl radical;

R$_3$ and R$_4$ are simultaneously CH$_3$;

or R$_3$ is H and R$_4$ is CH$_3$, CH$_2$CH$_3$, an isopropyl radical or phenyl radical;

R$_5$ is H, a C$_1$-C$_{24}$ alkyl radical, benzyl radical, phenethyl radical or 3-phenylpropanyl or 2,2-diphenylethanyl radical; and a pharmaceutically or cosmetically acceptable excipient.

2. The method according to claim 1, wherein said compound has a value of log P>4.

3. The method according to claim 1, wherein said compound has value of log P<3.5.

4. A method of propigmentation and depigmentation of skin which comprises administering to skin a composition containing at least one compound of general formula (I')

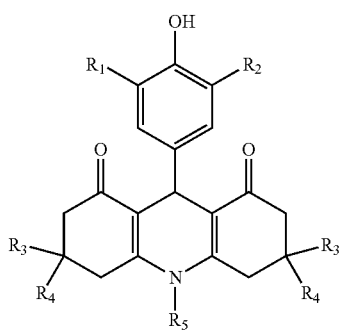

(I')

where:

R$_1$ and R$_2$ are simultaneously or independently H, OH, OCH$_3$ or a C$_1$-C$_5$ alkyl radical;

R$_3$ and R$_4$ are simultaneously CH$_3$;

or R$_3$ is H and R$_4$ is CH$_3$, CH$_2$CH$_3$ or phenyl radical;

R$_5$ is H, a C$_1$-C$_{24}$ alkyl radical, benzyl radical, phenethyl radical or 3-phenylpropanyl or 2,2-diphenylethanyl radical; and a pharmaceutically or cosmetically acceptable excipient.

5. The method according to claim 4, wherein said compound has a value of log P>4 as depigmenting agent.

6. The method according to claim 4, wherein said compound has a value of log P<3.5 as propigmenting agent.

7. A method of depigmenting of skin, head hair and/or body hair which comprises topically administering a composition containing at least one compound of general formula (I')

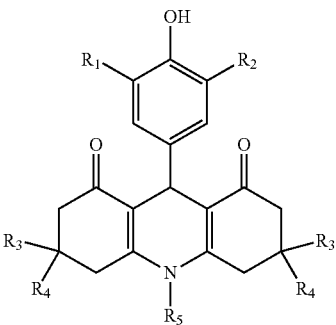

(I')

where:

R$_1$ and R$_2$ are simultaneously or independently H, OH, OCH$_3$ or a C$_1$-C$_5$ alkyl radical;

R$_3$ and R$_4$ are simultaneously CH$_3$;

or R$_3$ is H and R$_4$ is CH$_3$, CH$_2$CH$_3$, an isopropyl radical or phenyl radical;

R$_5$ is H, a C$_1$-C$_4$ alkyl radical, benzyl radical, phenethyl radical or 3-phenylpropanyl or 2,2-diphenylethanyl radical; and a pharmaceutically or cosmetically acceptable excipient.

* * * * *